(12) United States Patent
Safai

(10) Patent No.: US 8,761,338 B2
(45) Date of Patent: Jun. 24, 2014

(54) INTEGRATED BACKSCATTER X-RAY SYSTEM

(75) Inventor: Morteza Safai, Seattle, WA (US)

(73) Assignee: The Boeing Company, Chicago, IL (US)

( * ) Notice: Subject to any disclaimer, the term of this patent is extended or adjusted under 35 U.S.C. 154(b) by 213 days.

(21) Appl. No.: 13/164,583

(22) Filed: Jun. 20, 2011

(65) Prior Publication Data

US 2012/0321046 A1  Dec. 20, 2012

(51) Int. Cl.
*H05G 1/02* (2006.01)
*G01N 23/201* (2006.01)
*G01N 23/203* (2006.01)
*G21K 1/04* (2006.01)
*H01J 35/18* (2006.01)

(52) U.S. Cl.
CPC ........ *G01N 23/203* (2013.01); *G01N 2223/646* (2013.01); *G01N 2223/3301* (2013.01); *G21K 1/043* (2013.01); *H01J 35/18* (2013.01); *G01N 2223/631* (2013.01)
USPC ............................................. 378/86; 378/197

(58) Field of Classification Search
USPC ............. 378/197, 125, 86, 57, 62, 63, 87, 88; 250/358.1
See application file for complete search history.

(56) References Cited

U.S. PATENT DOCUMENTS

| | | | |
|---|---|---|---|
| 1,192,706 A * | 7/1916 | Thomson ........................ | 378/131 |
| 4,734,927 A | 3/1988 | Leguen et al. | |
| 4,780,901 A | 10/1988 | Gabbay et al. | |
| 5,237,598 A * | 8/1993 | Albert ........................... | 378/98.6 |
| 5,326,970 A | 7/1994 | Bayless | |
| 5,764,683 A | 6/1998 | Swift et al. | |
| 5,910,654 A | 6/1999 | Becker et al. | |
| 6,151,381 A | 11/2000 | Grodzins et al. | |
| 6,192,104 B1 | 2/2001 | Adams et al. | |
| 6,249,567 B1 | 6/2001 | Rothschild et al. | |
| 6,339,635 B1 | 1/2002 | Schardt et al. | |
| 6,396,901 B1 * | 5/2002 | Hell et al. ..................... | 378/130 |
| 6,453,007 B2 | 9/2002 | Adams et al. | |
| 6,459,761 B1 | 10/2002 | Grodzins et al. | |
| 6,459,764 B1 | 10/2002 | Chalmers et al. | |
| 6,621,888 B2 | 9/2003 | Grodzins et al. | |

(Continued)

FOREIGN PATENT DOCUMENTS

| | | |
|---|---|---|
| EP | 2275839 A2 | 1/2011 |
| GB | 2212975 A | 8/1989 |
| WO | WO2011008345 A2 | 1/2011 |

OTHER PUBLICATIONS

B. C. Towe and A. M. Jacobs. X-ray Backscatter Imaging, IEEE Transactions on Biomedical Engineering, vol. 2 BME-28, 9, 646-654 (1981).*

(Continued)

*Primary Examiner* — Irakli Kiknadze
(74) *Attorney, Agent, or Firm* — Yee & Associates, P.C.

(57) ABSTRACT

The different advantageous embodiments provide a method and apparatus for generating an x-ray beam. The x-ray beam is generated using an x-ray tube. The x-ray tube and a power supply are located inside of a housing connected to a moveable platform. A rotatable wheel connected to the moveable platform is rotated while the x-ray beam is being generated. The rotatable wheel has a number of apertures that allows at least a portion of the x-ray beam to pass through the rotatable wheel as the rotatable wheel rotates.

20 Claims, 8 Drawing Sheets

(56) References Cited

U.S. PATENT DOCUMENTS

| | | | |
|---|---|---|---|
| 6,658,087 B2 | 12/2003 | Chalmers et al. | |
| 7,010,094 B2 * | 3/2006 | Grodzins et al. | 378/157 |
| 7,174,001 B2 | 2/2007 | Andrews et al. | |
| 7,209,539 B2 * | 4/2007 | De Smet | 378/57 |
| 7,400,701 B1 | 7/2008 | Cason | |
| 7,463,714 B2 | 12/2008 | Edwards et al. | |
| 7,476,023 B1 * | 1/2009 | Canfield et al. | 378/203 |
| 7,508,910 B2 | 3/2009 | Safai et al. | |
| 7,529,343 B2 | 5/2009 | Safai et al. | |
| 7,535,990 B2 | 5/2009 | Safai et al. | |
| 7,564,948 B2 | 7/2009 | Wraight et al. | |
| 7,567,649 B1 | 7/2009 | Safai et al. | |
| 7,623,626 B2 | 11/2009 | Safai et al. | |
| 7,649,967 B2 | 1/2010 | Jonsson | |
| 7,649,976 B2 | 1/2010 | Georgeson et al. | |
| 7,839,969 B2 | 11/2010 | Gallup et al. | |
| 8,396,187 B2 | 3/2013 | Safai | |
| 2007/0206726 A1 | 9/2007 | Lu et al. | |
| 2009/0116614 A1 | 5/2009 | Kotowski et al. | |
| 2014/0064453 A1 | 3/2014 | Safai | |

OTHER PUBLICATIONS

"XRB401 Monoblock 200KV @ 400 Watts", Spellman High Voltage Electronics Corporation, pp. 1-3, Hauppage, New York. Retrieved Jun. 7, 2011. http://www.spellmanhv.cn/~/media/Files/Products/XRB401.ashx.

"High Voltage Power Supply and X-ray Generator Company", Spellman High Voltage Electronics Corporation, pp. 1-3. Retrieved Jun. 7, 2011. http://www.spellmanhv.com.

U.S. Appl. No. 12/965,159, Dec. 10, 2010, Safai.

U.S. Appl. No. 12/952,652, Nov. 23, 2010, Safai.

Extended European Search Report, dated Jul. 30, 2013, regarding Application No. EP12172727.5, 12 pages.

Safai et al., "System for Inspecting Objects Underwater", USPTO U.S. Appl. No. 13/286,795, filed Nov. 1, 2011, 38 pages.

Partial European Search Report, dated Apr. 12, 2013, regarding Application No. EP12172727.5, 8 pages.

"Products and Solutions: Securing Ports, Border Crossings and High-Threat Facilities and Events", American Science and Engineering, Inc., copyright 2011, 2 pages. Accessed Aug. 30, 2011, http://www.as-e.com/products_solutions/index.asp.

"Discussion of Methods for Underwater Bridge Inspection, Section 5: In-Depth Inspections", In: Bridge Inspection Manual, Texas Department of Transportation, Jul. 2002, 9 pages. Accessed Aug. 30, 2011, http://onlinemanuals.txdot.gov/txdotmanuals/ins/indepth_inspections.htm.

Shedlock et al., "X-Ray Backscatter Imaging for Aerospace Applications", AIP Conference Proceedings, vol. 1335, Jun. 2011, pp. 509-516.

Office Action, dated Feb. 28, 2014, regarding USPTO U.S. Appl. No. 13/286,795, 21 pages.

Ex Parte Quayle Action, dated Mar. 27, 2014, regarding USPTO U.S. Appl. No. 13/286,795, 10 pages.

\* cited by examiner

INTEGRATED BACKSCATTER X-RAY SYSTEM

BACKGROUND INFORMATION

1. Field

The present disclosure relates generally to x-ray systems and more specifically to backscatter x-ray systems.

2. Background

X-rays are frequently used to generate images for an object. X-rays are generated by an x-ray tube and directed at a surface of the object. Some of the x-rays may be reflected by the surface, while other x-rays may be absorbed. The x-rays that are reflected are frequently reflected by non-metallic surfaces. The x-rays that are absorbed are frequently absorbed by metallic surfaces. The reflected x-rays, also referred to as backscatter, may be collected to generate an image of the surface.

X-rays may also be used to identify inconsistencies in a surface of an object. For example, x-rays may be generated by an x-ray tube and directed at a metallic surface to identify inconsistencies in the metallic surface. One example of a metallic surface is a storage tank.

As the x-rays contact the metallic surface, an x-ray detector located on an opposite side of the surface may receive x-rays that travel through the metallic surface to the opposite side of the surface. In the event that the x-rays encounter an inconsistency in the metallic surface, some of the x-rays may be allowed to pass through the surface and be received by the x-ray detector. Thus, the x-rays that encounter the inconsistency are collected and an image is generated in which the inconsistency is visible.

In some examples, the surface may be located in an enclosed area. An enclosed area is an area that has no entrance through which an x-ray tube and/or x-ray detector may be inserted. Alternatively, the enclosed area may have an entrance, but the entry may be smaller than the size of the x-ray tube and/or the x-ray detector. As a result, a portion of a structure containing the surface in the enclosed area may need to be disassembled to allow access to the structure.

For example, when maintenance operations are performed, inspection of different portions of an aircraft may be performed. This inspection may include generating images of different surfaces on the aircraft to detect inconsistencies. As one illustrative example, the surface of an interior of a fuel tank may be inspected. With a fuel tank, access panels and/or other suitable components of an aircraft may be disassembled in order to gain access to the inside of the fuel tank. After the inspection occurs, the different parts may be reassembled or other operations may be performed on the fuel tank. These operations may increase the time and/or expense needed to perform maintenance operations.

Accordingly, it would be advantageous to have a method and apparatus which takes into account one or more of the issues discussed above, as well as possibly other issues.

SUMMARY

The different advantageous embodiments provide an apparatus comprising a moveable platform, a housing connected to the moveable platform, a power supply located inside of the housing, an x-ray tube located inside of the housing and a rotatable wheel. The rotatable wheel has a number of apertures. The rotatable wheel is connected to the moveable platform and is configured to rotate while the x-ray tube generates an x-ray beam such that the number of apertures allows at least a portion of the x-ray beam to pass through the rotatable wheel.

In another advantageous embodiment, a method for inspecting an object is provided. A moveable platform is positioned within a distance of the object to be inspected. The x-ray beam is generated using an x-ray tube. The x-ray tube and a power supply are located inside of a housing connected to a moveable platform, and wherein the x-ray beam travels the distance to the object. A rotatable wheel connected to the moveable platform is rotated while the x-ray beam is being generated. The rotatable wheel has a number of apertures that allows at least a portion of the x-ray beam to pass through the rotatable wheel as the rotatable wheel rotates. A backscatter is detected in response to the at least the portion of the x-ray beam encountering an object. The backscatter comprises x-rays in the at least the portion of the x-ray beam that are reflected off of a surface of the object. A number of images is generated using the backscatter for use in determining whether a number of inconsistencies is present on the surface of the object.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
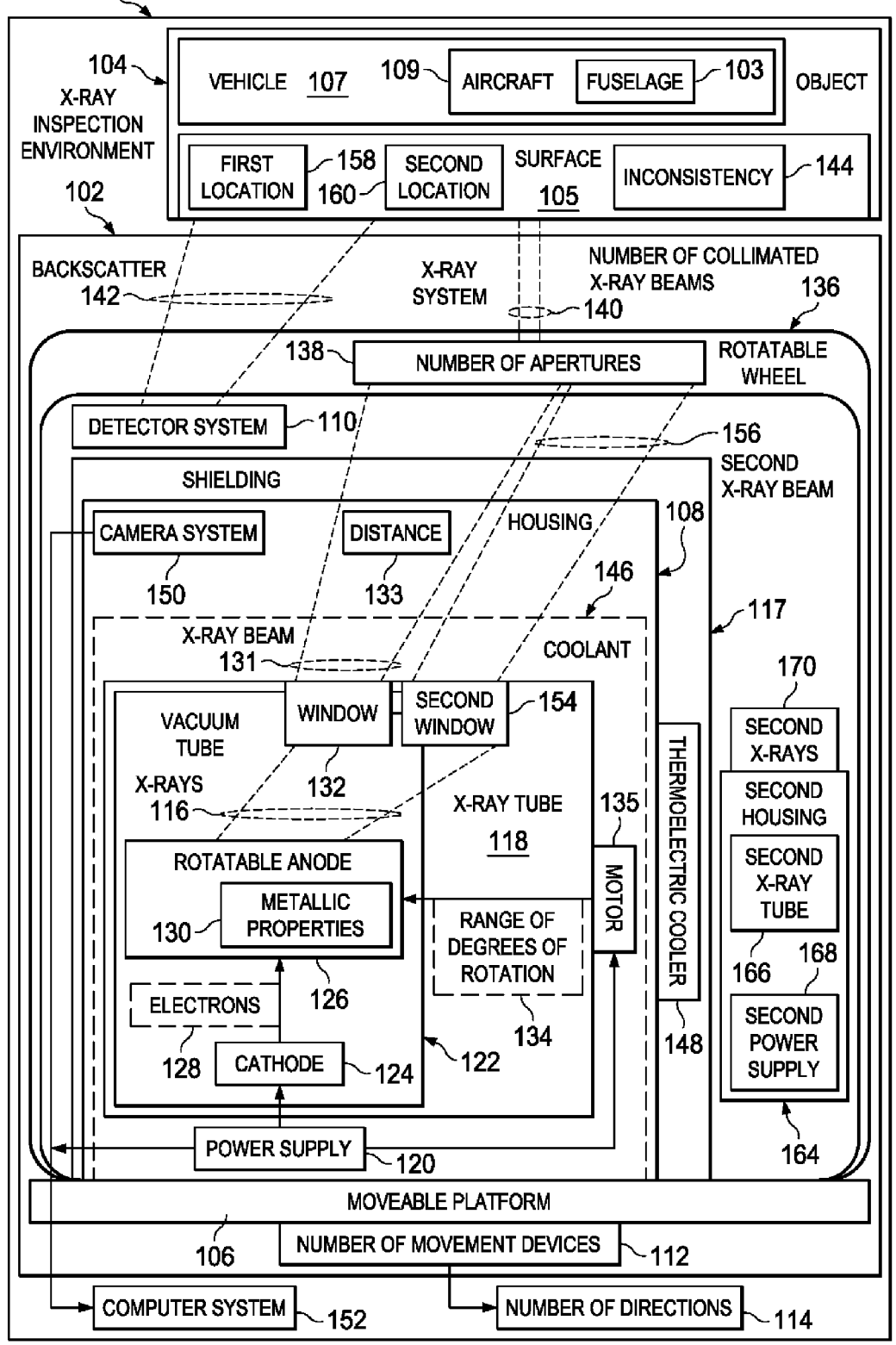
FIG. 1 is an illustration of an x-ray inspection environment in accordance with an advantageous embodiment.

The different advantageous embodiments recognize and take into account a number of different considerations. As used herein, a number of items means one or more items. For example, a number of different considerations means one or more considerations.

The different advantageous embodiments recognize and take into account that testing a surface for inconsistencies is desirable. For example, an inconsistency in a surface of an object may cause the object to not perform properly or not perform for the intended purpose of the object. For example, a wheel with an inconsistency may be unable to retain air pressure for a desired period of time.

However, such a surface may be located within a structure that is difficult and time-consuming to disassemble. For example, the surface may be the inside of a fuel tank located within an aircraft. Disassembly of a portion of the aircraft and/or the fuel tank to access the inside of the fuel tank for inspection and testing may be more expensive and time-consuming than desired.

The different advantageous embodiments also recognize and take into account that even when a surface is accessible for testing and inspection, accessing an opposite side of the surface may be more difficult or time-consuming than desired. The opposite side of the surface is used to position an x-ray detector such that an inconsistency in the surface would allow x-rays to pass through the surface and be received by the x-ray detector.

Additionally, the different advantageous embodiments recognize and take into account that some objects may not be disassembled for testing and inspection. For example, a pipe may not be disassembled for inspection and testing of the interior surface of the pipe.

Further, the different advantageous embodiments take into account and recognize that currently available x-ray systems that use backscattering comprise an x-ray tube and components external to the x-ray tube. Backscattering is the projection of x-rays towards a surface and the identification of a response comprising x-rays reflected off of the surface. These x-ray systems may comprise more components external to the x-ray tube than desired.

For example, currently available x-ray systems that use backscattering may require a power supply of about 160 kiloelectron volts (KeV) for the x-ray tube. Components external to an x-ray tube requiring this amount of power may include, for example, without limitation, a high voltage power cable, an external cooling system, a number of electronics racks, a communications cable, metal tracks, cable management chains, and/or other suitable components.

As a result, these components may increase the weight and/or size of an x-ray system more than desired. As one illustrative example, a conventional x-ray system that uses backscattering may weigh about 1400 pounds. The different advantageous embodiments recognize and take into account that moving an x-ray system of this weight may take more time and/or effort than desired.

Further, the different advantageous embodiments recognize and take into account that the larger sizes for currently available x-ray systems may make moving these x-ray systems to different locations more difficult than desired. For example, these x-ray systems may need to be disassembled at one location and reassembled at another location for use. This disassembly and/or reassembly may take more time and/or effort than desired and may reduce use of this type of system.

Thus, the different advantageous embodiments provide a method and apparatus for generating x-rays. In one advantageous embodiment, an apparatus comprises a moveable platform, a housing connected to the moveable platform, a power supply located inside of the housing, an x-ray tube located inside of the housing, and a rotatable wheel connected to the moveable platform. The rotatable wheel has a number of apertures and is configured to rotate while the x-ray tube generates an x-ray beam such that the number of apertures allows at least a portion of the x-ray beam to pass through the rotatable wheel.

With reference now to FIG. 1, an illustration of an x-ray inspection environment is depicted in accordance with an advantageous embodiment. In these illustrative examples, x-ray inspection environment 100 includes x-ray system 102 and object 104. In these illustrative examples, object 104 may take the form of, for example, fuselage 103 of vehicle 107. Vehicle 107 may be aircraft 109 in some advantageous embodiments. In one illustrative example, x-ray system 102 may be used to perform an inspection of surface 105 of object 104.

As depicted, x-ray system 102 includes moveable platform 106, housing 108 connected to moveable platform 106, and detector system 110. As used herein, a first component "connected to" a second component means that the first component can be connected directly or indirectly to the second component. In other words, additional components may be present between the first component and the second component. The first component is considered to be indirectly connected to the second component when one or more additional components are present between the two components. When the first component is directly connected to the second component, no additional components are present between the two components.

Moveable platform 106 takes the form of any platform configured to move over a surface. For example, moveable platform 106 may be a cart. Moveable platform 106 may have number of movement devices 112 connected to moveable platform 106. Number of movement devices 112 allows moveable platform 106 to move over a surface in number of directions 114.

Number of movement devices 112 may include, for example, at least one of a number of wheels, a number of rollers, a number of runners, a number of sliders, a propulsion system, and/or other suitable movement devices. In some illustrative examples, a human operator may move moveable platform 106 using number of movement devices 112. For example, when moveable platform 106 is a cart with wheels and/or rollers connected to the cart, a human operator may push the cart to move the cart. In these advantageous embodiments, moveable platform 106 is positioned within distance 133 of object 104 to perform inspection of object 104. Distance 133 is an amount of space that is within the maximum range of x-ray beam 131 generated by x-ray tube 118. In other words, x-ray beam 131 may travel across distance 133 to encounter object 104.

As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example also may include item A, item B, and item C, or item B and item C.

In these illustrative examples, housing 108 is configured to house components needed for generating x-rays 116. X-rays 116 are waves in the electromagnetic spectrum that have wavelengths from about 0.01 nanometers to about ten nanometers. X-rays 116 form electromagnetic radiation referred to as x-radiation. Further, housing 108 may be formed from a number of materials that allow x-rays 116 to pass through housing 108. Shielding 117 may be provided around sections of housing 108 at which x-rays 116 passing through housing 108 is not desired. Shielding 117 is a material that substantially prevents x-rays from passing through shielding 117. In these advantageous embodiments, shielding 117 absorbs x-rays 116 at locations on housing 108 at which shielding 117 is located. For example, shielding 117 may be composed at least partially of lead.

As depicted, x-ray tube 118 and power supply 120 are located inside of housing 108. X-ray tube 118 may include, for example, without limitation, vacuum tube 122, cathode 124, and rotatable anode 126. In these depicted examples, cathode 124 and rotatable anode 126 are located inside of vacuum tube 122 in these examples.

Cathode 124 emits electrons 128. Vacuum tube 122 is configured to accelerate electrons 128 emitted from cathode 124 such that electrons 128 collide with rotatable anode 126. In particular, rotatable anode 126 is configured to generate x-rays 116 in response to receiving electrons 128 emitted by cathode 124. Rotatable anode 126 has metallic properties 130 that cause x-rays 116 to be generated in response to electrons 128 colliding with rotatable anode 126. For example, rotatable anode 126 may be made up at least partially of rhodium or tungsten.

X-rays 116 generated by rotatable anode 126 are generated in a particular direction in these illustrative examples. In this advantageous embodiment, x-rays 116 generated by rotatable anode 126 travel toward window 132. A portion of x-rays 116 pass through window 132 and out of vacuum tube 122. Window 132 is a material that allows the portion of x-rays 116 to pass through window 132 and outside housing 108. Window 132 may be composed of beryllium, glass, aluminum, or another suitable material. The portion of x-rays 116 that pass through window 132 forms x-ray beam 131. In these depicted examples, window 132 may also be referred to as a beam port on vacuum tube 122. A portion of x-ray beam 131 may have a higher or lower intensity than another portion of x-ray beam 131. For example, the center of x-ray beam 131 may have the highest intensity in x-ray beam 131.

Additionally, rotatable anode 126 is configured to rotate. In particular, motor 135 is configured to rotate rotatable anode 126. Motor 135 is located outside of vacuum tube 122 and inside of housing 108.

Rotatable anode 126 may be rotated within range of degrees of rotation 134. Range of degrees of rotation 134 may include, for example, from about zero degrees of rotation to about 180 degrees of rotation. The position to which rotatable anode 126 is rotated determines the direction for x-ray beam 131. Changing the direction in which x-rays 116 are generated may also change the location and/or direction of the portion of x-ray beam 131 having the highest intensity in x-ray beam 131.

In these illustrative examples, x-ray system 102 includes rotatable wheel 136 connected to moveable platform 106. Housing 108 is positioned within an interior of rotatable wheel 136. Rotatable wheel 136 has number of apertures 138. Each aperture is a hole or opening in rotatable wheel 136.

Rotatable wheel 136 is configured to rotate while x-ray tube 118 generates x-rays 116. Rotatable wheel 136 may rotate about 360 degrees in these depicted examples. As rotatable wheel 136 rotates, number of apertures 138 in rotatable wheel 136 also rotates. A portion of x-ray beam 131 is allowed to pass through one or more of number of apertures 138 as rotatable wheel 136 rotates. The portion of x-ray beam 131 that passes through an aperture in number of apertures 138 forms an x-ray beam that is collimated in a direction through the aperture. In the advantageous embodiments, collimating a portion of x-ray beam 131 means causing the rays of the portion of x-ray beam 131 to be substantially parallel in direction. In some advantageous embodiments, collimating the portion of x-ray beam 131 also includes reducing the radius of the portion of x-ray beam 131. In particular, the portion of x-ray beam 131 that passes through the aperture is a collimated x-ray beam. In this manner, number of collimated x-ray beams 140 may be formed as rotatable wheel 136 rotates, while x-rays 116 are being generated. Additionally, rotatable anode 126 may be rotated to direct the portion of x-ray beam 131 having the highest intensity toward the center of an aperture in number of apertures 138.

In these illustrative examples, each of number of collimated x-ray beams 140 is directed towards a particular location on surface 105 of object 104. A speed of rotation for rotatable wheel 136 may be controlled such that number of collimated x-ray beams 140 reaches locations on surface 105 of object 104 at times based on a selected time interval.

A portion of each of number of collimated x-ray beams 140 that encounters surface 105 is absorbed by object 104, while another portion is reflected off of surface 105. The portion of an x-ray beam that is reflected is referred to as backscatter 142.

Detector system 110 in x-ray system 102 is configured to detect backscatter 142 that is formed in response to x-ray beams in number of collimated x-ray beams 140 encountering surface 105 of object 104. In particular, backscatter 142 is formed by x-rays within number of collimated x-ray beams 140 reflecting off of surface 105 when the x-rays encounter surface 105.

In this illustrative example, number of collimated x-ray beams 140 may encounter inconsistency 144 on surface 105 of object 104. When number of collimated x-ray beams 140 encounters inconsistency 144 on surface 105, backscatter 142 may be formed in a direction that is not detected by detector system 110.

Detector system 110 may take a number of different forms and comprise any number of detectors. For example, detector system 110 may comprise any number of scintillator detectors, solid state detectors, and/or other suitable types of detectors.

Number of apertures 138 may be different sizes in different advantageous embodiments. For example, in a first advantageous embodiment, number of apertures 138 may be a first size that allows a particular amount of a collimated x-ray beam in number of collimated x-ray beams 140 to pass through each of number of apertures 138 in a particular time period. In other words, a particular number of x-ray photons are allowed to pass through each of number of apertures 138. In a second advantageous embodiment, number of apertures 138 may be a second size that is larger than the first size in the first advantageous embodiment. Number of apertures 138 of the second size allows more of the collimated x-ray beam in number of collimated x-ray beams 140 or x-ray photons to pass through each of number of apertures 138 in the particular time period than number of apertures 138 of the first size. Thus, a greater amount of number of collimated x-ray beams 140 is reflected to form backscatter 142. Images generated, using backscatter 142 in the second advantageous embodiment, may have greater contrast as compared to images generated using backscatter 142 in the first advantageous embodiment.

In these illustrative examples, x-ray tube 118 is powered by power supply 120 in housing 108. Power supply 120 may also provide power to motor 135 to rotate rotatable anode 126 and/or number of movement devices 112 to move moveable platform 106. Integrating power supply 120 and x-ray tube 118 into housing 108 reduces a need for providing shielding for both power supply 120 and x-ray tube 118.

Further, with power supply 120 and x-ray tube 118 in housing 108, a single cooling system may be used to cool both power supply 120 and x-ray tube 118 in housing 108. The single cooling system does not conduct electricity in these advantageous embodiments. For example, the cooling system may take the form of coolant 146. Coolant 146 may be present inside of housing 108. Coolant 146 may be a non-conductive liquid in which power supply 120 and x-ray tube 118 are both immersed. The non-conductive liquid may be an oil, such as, for example, without limitation, mineral oil or liquid petroleum. In some illustrative examples, thermoelectric cooler 148 may be attached to housing 108 to keep the oil cool.

In some illustrative examples, camera system 150 may be located inside of housing 108. Camera system 150 may include, for example, a processor unit and a number of cameras. Camera system 150 may be configured to generate images for surface 105 of object 104 using backscatter 142 and/or generate images of an area in x-ray inspection environment 100 around x-ray system 102.

As one illustrative example, images of the area around x-ray system 102 may take the form of, for example, photographs, video, infrared images, and/or other suitable types of images. These images may be used to control movement of moveable platform 106.

Images for surface 105, generated using backscatter 142, may be stored in camera system 150 and transmitted wirelessly to computer system 152. Computer system 152 may be located remotely to x-ray system 102 for processing. In other illustrative examples, computer system 152 may be in communication with x-ray system 102 and configured to generate images for surface 105 of object 104 using backscatter 142.

In these illustrative examples, the resolution for the images generated using backscatter 142 may be controlled by controlling the speed of rotation for rotatable wheel 136. For example, a slower speed of rotation for rotatable wheel 136 may allow images to be generated with a higher contrast and/or lower resolution as compared to a faster speed of rotation. Further, a faster speed of rotation for rotatable wheel 136 may allow images to be generated with a higher resolution as compared to a slower speed of rotation.

The amount of electrical current used to generate x-rays 116 may also be changed in some advantageous embodiments. A higher amount of electrical current used to generate x-rays 116 may allow images to be generated with a higher contrast as compared to images generated using x-rays 116 with a lower amount of electrical current. Thus, in some advantageous embodiments, the amount of electrical current may be increased as the speed of rotation of rotatable wheel 136 is increased to reach the same or similar level of contrast in generated images as compared to images generated with a lower electrical current and/or a lower speed of rotation for rotatable wheel 136.

Additionally, in these illustrative examples, moveable platform 106 may be moved in a direction in number of directions 114 that is substantially perpendicular to a direction of rotation for rotatable wheel 136. In other words, moveable platform 106 moves in a direction in number of directions 114 along an axis. Rotatable wheel 136 may be rotated about this axis while moveable platform 106 moves in a direction along the axis. In this manner, images may be generated in a grid-type pattern for object 104.

In some illustrative examples, second window 154 may be present on vacuum tube 122. Second window 154 may be positioned substantially opposite to window 132. Second x-ray beam 156 is allowed to pass through second window 154. Second x-ray beam 156 may have a direction substantially opposite to the direction for x-ray beam 131. In such an advantageous embodiment, rotatable anode 126 may be rotated to generate x-ray beam 131 traveling through window 132 in a first direction, and computer system 152 may generate images using backscatter 142 from the first direction. Rotatable anode 126 may then be rotated to generate second x-ray beam 156 traveling though second window 154. Thus, x-ray system 102 nor housing 108 may not be moved to generate images from two substantially opposite objects.

Rotation of rotatable wheel 136 may allow x-ray beam 131 to pass through number of apertures 138 to first location 158 on surface 105 and second x-ray beam 156 to pass through number of apertures 138 to second location 160 on surface 105. Further, first location 158 and second location 160 may be substantially opposite to each other in these illustrative examples.

In one illustrative example, when object 104 is a fuselage for an aircraft, first location 158 and second location 160 may be locations substantially opposite to each other inside the fuselage. In this manner, when window 131 and second window 154 are both present, x-ray system 102 may be used to inspect locations that are substantially opposite to each other at the same time.

In still other illustrative examples, second housing 164 may be connected to moveable platform 106 and positioned within the interior of rotatable wheel 136. Second housing 164 may be configured similar to housing 108. For example, second x-ray tube 166 and second power supply 168 may be located inside of second window 154. Second x-ray tube 166 is configured to generate second x-rays 170.

As rotatable wheel 136 rotates, number of apertures 138 in rotatable wheel 136 allows x-rays 116 to pass through rotatable wheel 136 to first location 158 on surface 105 of object 104 and second x-rays 170 to pass through rotatable wheel 136 to second location 160 on surface 105 of object 104.

The illustration of x-ray inspection environment 100 in FIG. 1 is not meant to imply physical or architectural limitations to the manner in which different advantageous embodiments may be implemented. Other components in addition and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in other illustrative examples, object 104 may be some other object other than a fuselage of an aircraft. Object 104 may be selected from one of, for example, without limitation, a hull of a ship, a storage tank, a fuel tank, a structure on a space shuttle, a cryogenic tank, a trailer for a truck, a train car, a container, an engine nacelle, or some other suitable type of structure.

In some illustrative examples, additional components may be present in housing 108 in addition to power supply 120, x-ray tube 118, coolant 146, and camera system 150. As one illustrative example, computer system 152 may be located inside of the housing. In this illustrative example, camera system 150 may not be present. Computer system 152 is configured to generate images using backscatter 142. Housing 108 may also contain a laser system that projects a laser beam on object 104. The laser beam may be projected at the location that number of collimated x-ray beams 140 are encountering object 104. In another advantageous embodiment, the laser beam may be projected at a location that number of collimated x-ray beams 140 will encounter object 104 at a future point in time.

Figure 2:
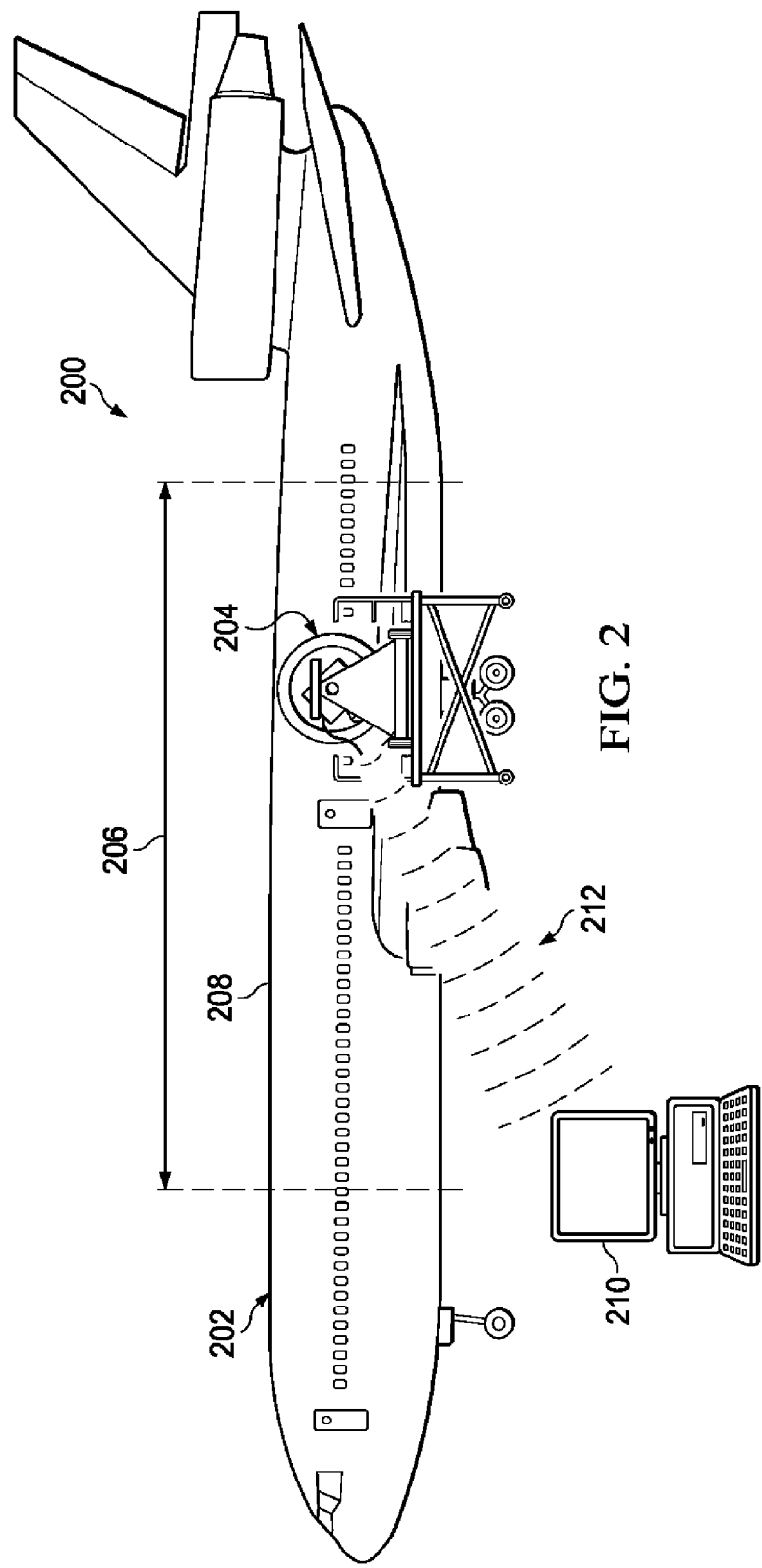
FIG. 2 is an illustration of an x-ray inspection environment in accordance with an advantageous embodiment.

With reference now to FIG. 2, an illustration of an x-ray inspection environment is depicted in accordance with an advantageous embodiment. In this illustrative example, x-ray inspection environment 200 is an example of one implementation for x-ray inspection environment 100 in FIG. 1.

As depicted, x-ray inspection environment 200 includes aircraft 202 and x-ray system 204. Section 206 of fuselage 208 is an example of one implementation for object 104 in FIG. 1. X-ray system 204 is an example of one implementation for x-ray system 102 in FIG. 1.

In this illustrative example, x-ray system 204 generates images for an interior of section 206 of fuselage 208 of aircraft 202. These images may be used to identify, for example, any inconsistencies that may be present in section 206 of fuselage 208.

In particular, x-ray system 204 is configured to move within fuselage 208 and generate x-rays as x-ray system 204 moves. A portion of the x-rays generated may encounter a surface of the interior of section 206 of fuselage 208 and be reflected off of the surface. X-ray system 204 is configured to detect this backscatter formed in response to the portion of x-rays that encounter this surface.

In this illustrative example, x-ray system 204 generates images using the backscatter detected. These images may be sent to computer system 210 for processing using wireless communications link 212. For example, computer system 210 may process these images to determine whether any inconsistencies are present on a surface of the interior of section 206 of fuselage 208.

Figure 3:
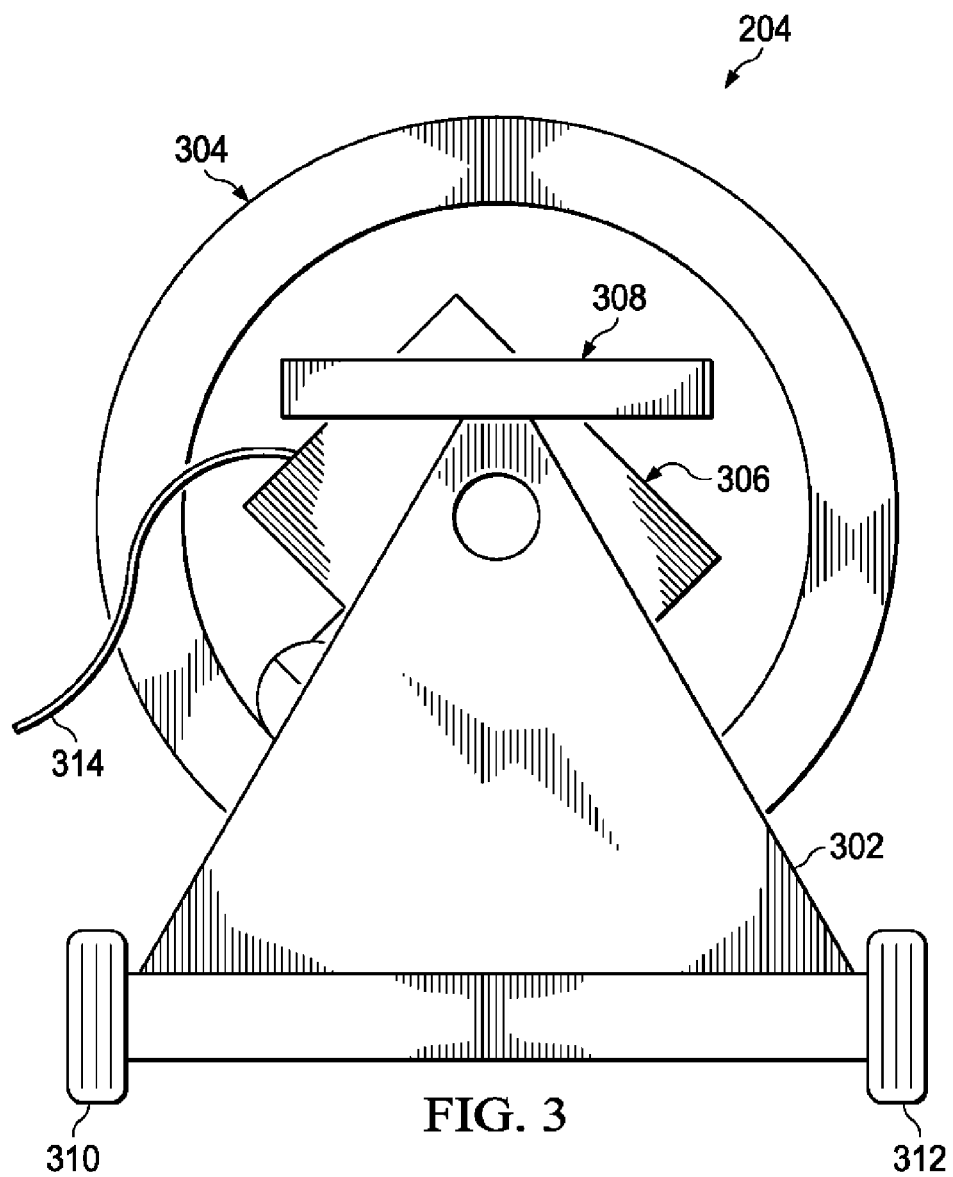
FIG. 3 is an illustration of a front view of an x-ray system in accordance with an advantageous embodiment.

With reference now to FIG. 3, an illustration of a front view of an x-ray system is depicted in accordance with an advantageous embodiment. In this illustrative example, x-ray system 204 from FIG. 2 is depicted in more detail.

As depicted, x-ray system 204 includes moveable platform 302, rotatable wheel 304, housing 306, and detector system 308. Moveable platform 302 has wheel 310, wheel 312, and two additional wheels (not shown in this view) connected to moveable platform 302. These wheels allow moveable platform 302 to move.

In this illustrative example, moveable platform 302 is connected to rotatable wheel 304. Additionally, moveable platform 302 is connected to housing 306. As illustrated, housing 306 is positioned within an interior of rotatable wheel 304. Housing 306 houses components configured to generate x-rays. Power may be supplied to the components located inside of housing 306 through power cable 314, in this depicted example.

Figure 4:
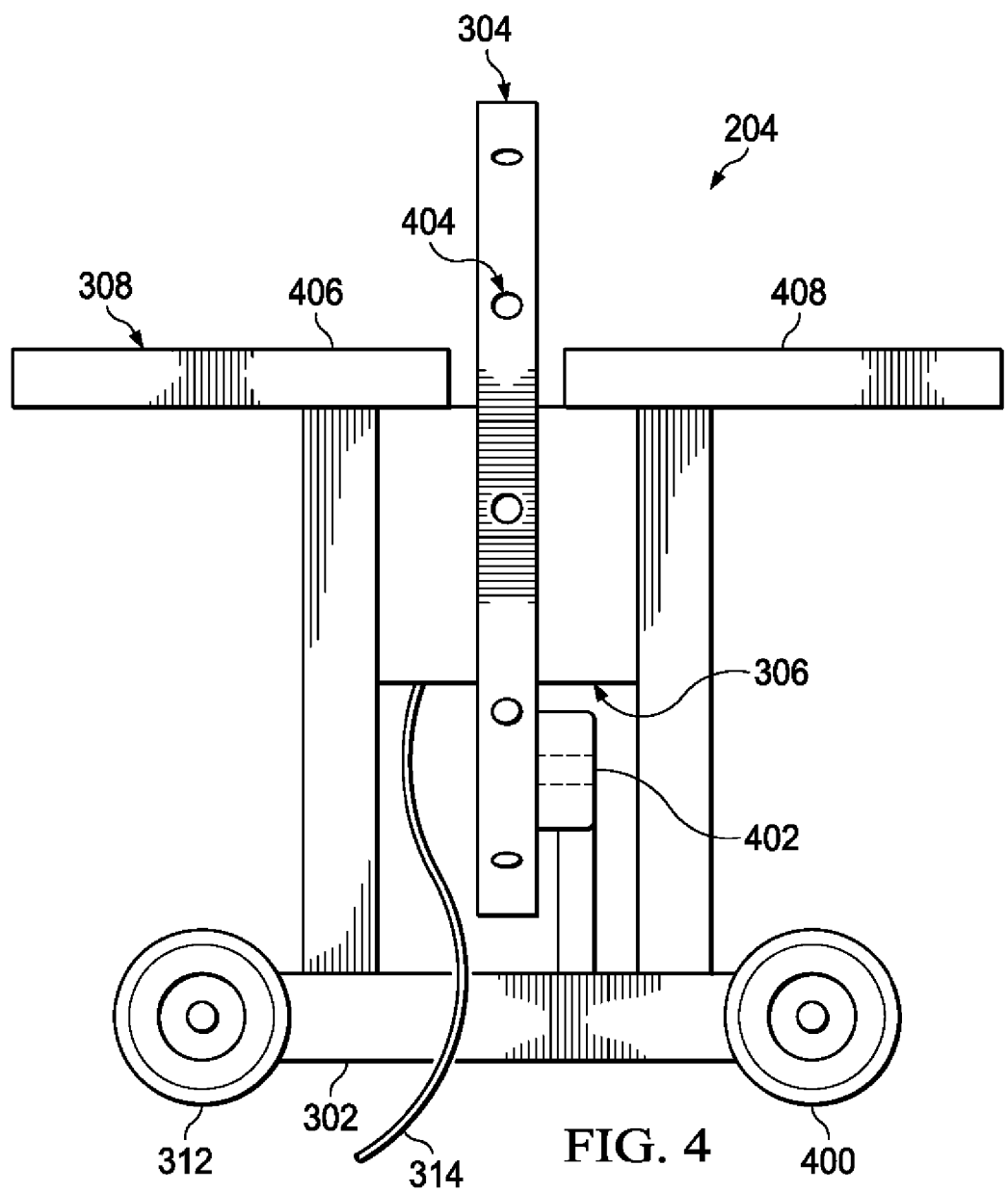
FIG. 4 is an illustration of a side view of an x-ray system in accordance with an advantageous embodiment.

With reference now to FIG. 4, an illustration of a side view of an x-ray system is depicted in accordance with an advantageous embodiment. In this illustrative example, a side view of x-ray system 204 from FIGS. 2-3 is depicted.

As depicted, wheel 400 is connected to moveable platform 302 in addition to wheel 312, wheel 310 from FIG. 3, and another wheel (not shown in this view). Further, in this illustrative example, rotatable wheel 304 is connected to moveable platform 302 through motor system 402. Motor system 402 is configured to rotate rotatable wheel 304. In this illustrative example, rotatable wheel 304 may be rotated about 360 degrees.

Further, rotatable wheel 304 has apertures 404. Apertures 404 allow x-rays generated by components in housing 306 to pass through rotatable wheel 304. Additionally, detector system 308 has detector 406 and detector 408. These two detectors are scintillator detectors configured to detect backscatter formed in response to x-rays being reflected off of a surface.

Figure 5:
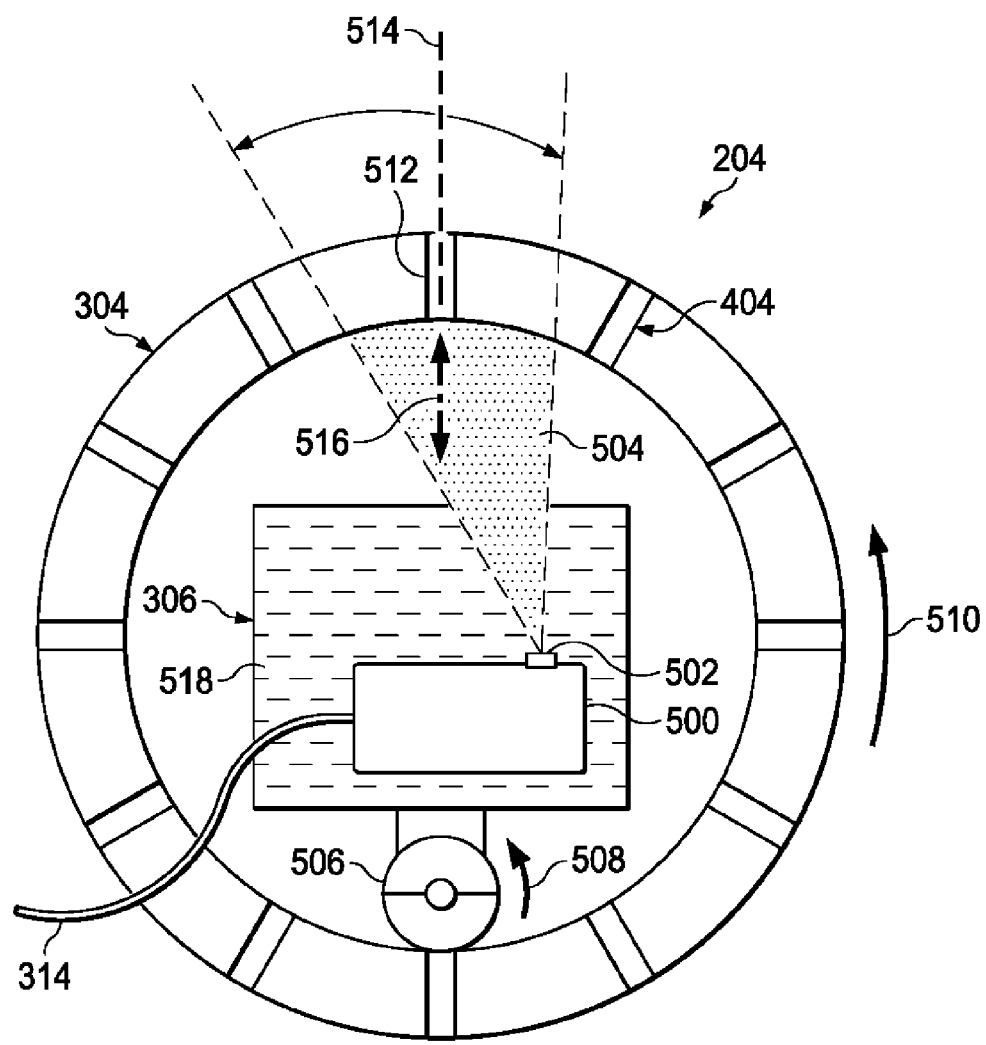
FIG. 5 is an illustration of a portion of an x-ray system in accordance with an advantageous embodiment.

With reference now to FIG. 5, an illustration of a portion of an x-ray system is depicted in accordance with an advantageous embodiment. In this illustrative example, x-ray system 204 from FIGS. 2-4 is depicted without moveable platform 302 and detector system 308 from FIGS. 3-4. Apertures 404 for rotatable wheel 304 are depicted in phantom view in this figure.

As illustrated, x-ray tube 500 is located inside of housing 306. X-ray tube 500 is configured to generate x-rays that pass through x-ray tube 500 at window 502. The x-rays that pass through window 502 form x-ray beam 504 in this illustrative example. X-ray tube 500 receives power through power cable 314 connected to x-ray tube 500 inside of housing 306. In this manner, power cable 314 is a power supply for x-ray tube 500 inside of housing 306.

Further, motor system 506 is connected to housing 306 in this depicted example. Motor system 506 is configured to turn in the direction of arrow 508 to rotate housing 306.

In some illustrative examples, x-ray tube 500 may be connected to housing 306 such that rotation of housing 306 in the direction of arrow 508 rotates x-ray tube 500 with housing 306 in the direction of arrow 508. X-ray tube 500 is rotated such that a direction of x-ray beam 504 changes. In other illustrative examples, motor system 506 or some other motor system (not shown) may be configured to rotate x-ray tube 500 and/or a rotatable anode in x-ray tube 500 while housing 306 rotates.

In this illustrative example, rotatable wheel 304 is configured to rotate in the direction of arrow 510. As rotatable wheel 304 rotates, apertures 404 also rotate. Apertures 404 allow a portion of x-ray beam 504 to pass through rotatable wheel 304. As one illustrative example, a portion of x-ray beam 504 passes through aperture 512 in the form of collimated x-ray beam 514. Collimated x-ray beam 514 travels in a direction along axis 516 through aperture 512.

As rotatable wheel 304 rotates in the direction of arrow 510, the portion of x-ray beam 504 that forms collimated x-ray beam 514 passing through aperture 512 may change. In some illustrative examples, motor system 506 may be configured to rotate housing 306 while rotatable wheel 304 rotates such that the portion of x-ray beam 504 that forms collimated x-ray beam 514 passing through aperture 512 remains substantially the same.

In this illustrative example, coolant 518 is present in housing 306. In particular, x-ray tube 500 and the portion of power cable 314 located inside of housing 306 are immersed in coolant 518. Coolant 518 may be a non-conductive oil. A thermoelectric cooler (not shown in this view) may be attached to housing 306 to keep coolant 518 cool during operation of x-ray system 204.

Figure 6:
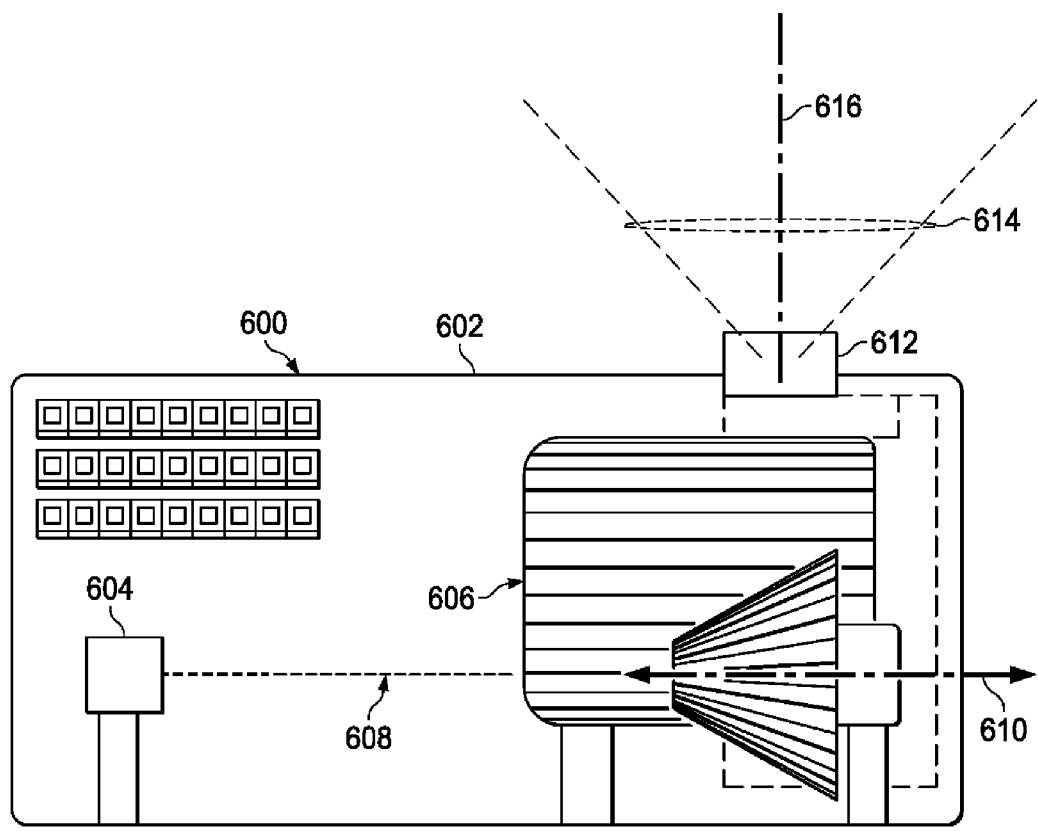
FIG. 6 is an illustration of a side view of an x-ray tube in accordance with an advantageous embodiment.

With reference now to FIG. 6, an illustration of a side view of an x-ray tube is depicted in accordance with an advantageous embodiment. X-ray tube 600 is an example of one implementation for x-ray tube 118 in FIG. 1.

X-ray tube 600 takes the form of vacuum tube 602. Vacuum tube 602 has cathode 604 that is configured to emit electrons 608 that collide with rotatable anode 606. Rotatable anode 606 generates x-rays in response to receiving electrons 608.

In this illustrative example, rotatable anode 606 is configured to rotate about axis 610. As depicted, the portion of x-rays generated by rotatable anode 606 that pass through window 612 for housing vacuum tube 602 form x-ray beam 614. X-ray beam 614 travels in a direction along axis 616 in this depicted example.

As rotatable anode 606 rotates about axis 610, the angle at which electrons 608 collide with rotatable anode 606 changes. Thus, the direction in which x-ray beam 614 travels may be changed by rotating rotatable anode 606.

Figure 7:
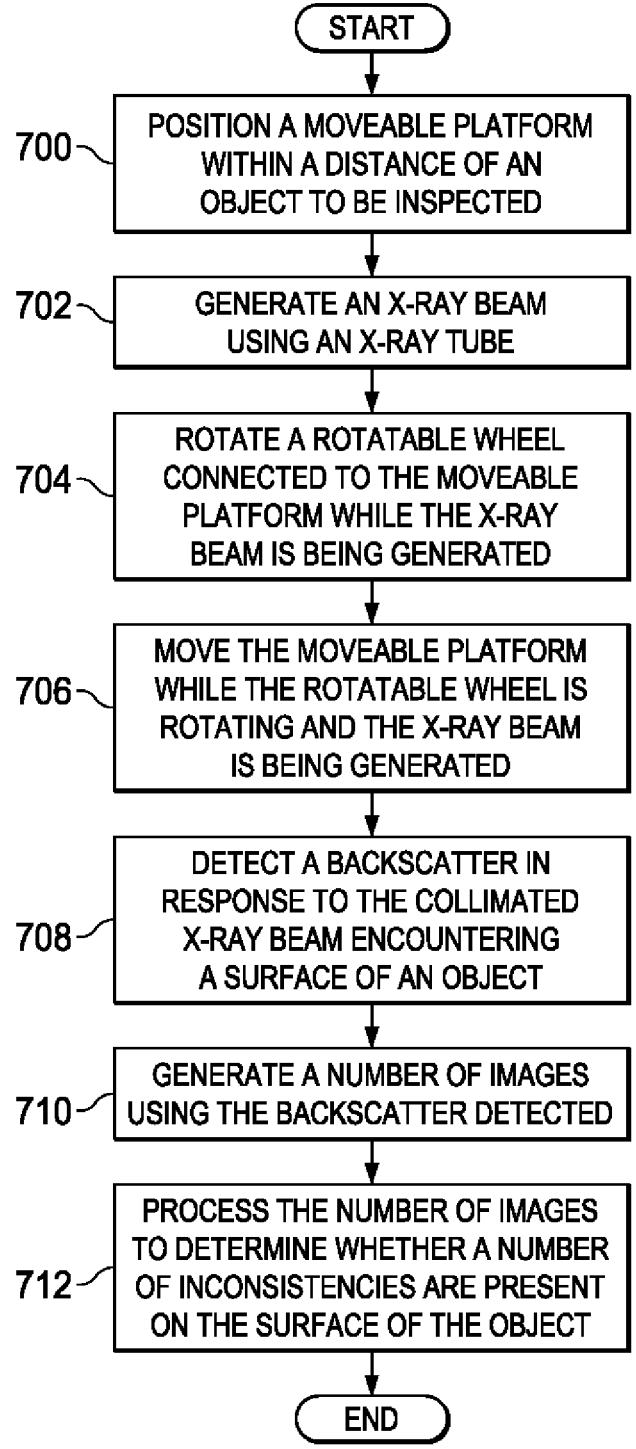
FIG. 7 is an illustration of a flowchart of a process for generating x-rays in accordance with an advantageous embodiment.

With reference now to FIG. 7, an illustration of a flowchart of a process for generating x-rays is depicted in accordance with an advantageous embodiment. The process illustrated in FIG. 7 may be implemented using x-ray system 102 in FIG. 1.

As depicted, a moveable platform is positioned within a distance of an object to be inspected (operation 700). The distance is an example of distance 133 in FIG. 1. In other words, the moveable platform is positioned within a range that may be traveled by x-rays generated by the x-ray tube connected to the moveable platform. In this advantageous embodiment, the distance is a distance to a surface of the object to be inspected. The moveable platform may be positioned by a human operator, by operation of a motor, or another suitable method.

An x-ray beam is then generated using an x-ray tube (operation 702). The x-ray tube and a power supply are located inside of a housing connected to the moveable platform. The moveable platform is configured to move such that the housing and the x-ray tube in the housing move.

The process then rotates a rotatable wheel connected to the moveable platform while the x-ray beam is being generated (operation 704). The rotatable wheel has a number of apertures that allow at least a portion of the x-ray beam to pass through the rotatable wheel as the rotatable wheel rotates. The portion of the x-ray beam that passes through an aperture may be referred to as a collimated x-ray beam.

Further, the process moves the moveable platform while the rotatable wheel is rotating and the x-ray beam is being generated (operation 706). In this illustrative example, rotation of the rotatable wheel may be about an axis in which the moveable platform moves along a direction of this axis.

Thereafter, the process detects a backscatter in response to the collimated x-ray beam encountering a surface of an object (operation 708). In particular, the backscatter is formed by a portion of the x-rays in the collimated x-ray beam reflecting off of the surface of the object in response to the x-rays encountering the surface.

The process then generates a number of images using the backscatter detected (operation 710). The number of images may be generated in a grid-type pattern when the moveable platform is moved and the rotatable wheel is rotated at the same time while the x-rays are being generated by the x-ray tube. Next, the number of images are processed to determine whether a number of inconsistencies are present on the surface of the object (operation 712), with the process terminating thereafter.

The flowcharts and block diagrams in the different depicted embodiments illustrate the architecture, functionality, and operation of some possible implementations of apparatus and methods in an advantageous embodiment. In this regard, each block in the flowchart or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

Figure 8:
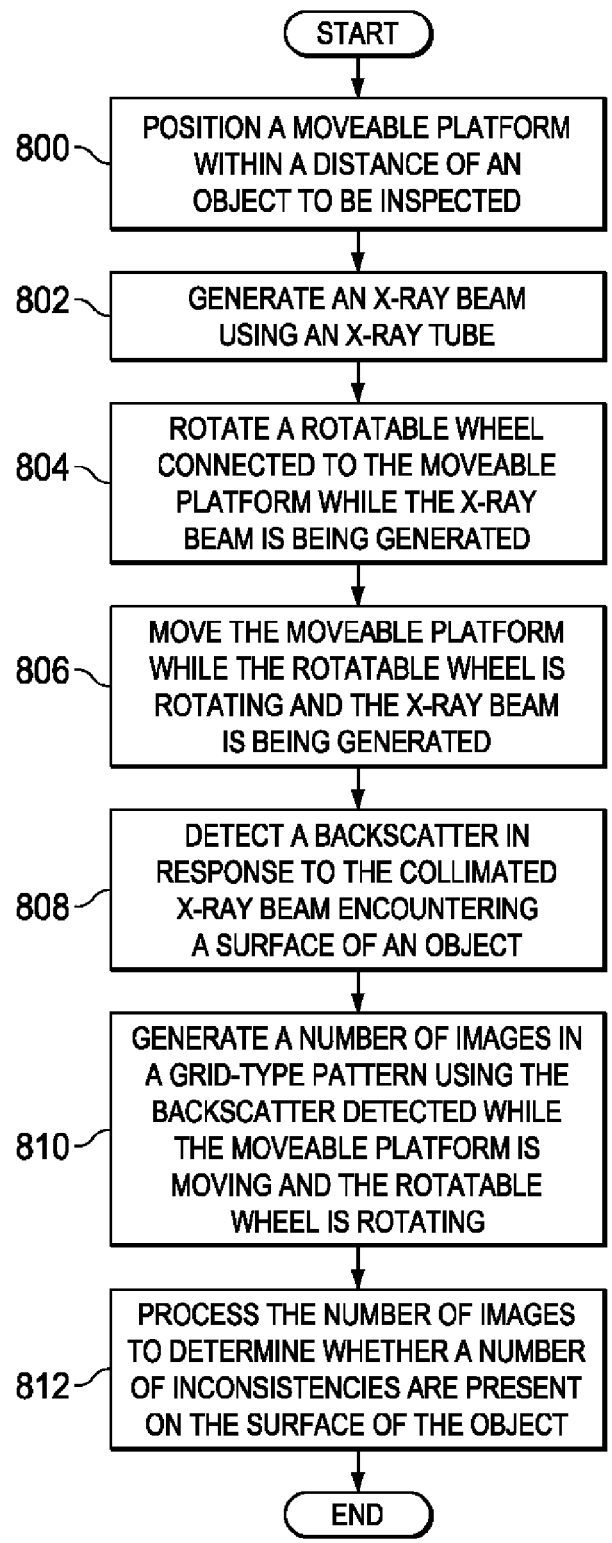
FIG. 8 is an illustration of a flowchart of a process for generating x-rays in accordance with an advantageous embodiment.

With reference now to FIG. 8, an illustration of a flowchart of a process for generating x-rays is depicted in accordance with an advantageous embodiment. The process illustrated in FIG. 8 may be implemented using x-ray system 102 in FIG. 1.

As depicted, a moveable platform is positioned within a distance of an object to be inspected (operation 800). The distance is an example of distance 133 in FIG. 1. In other words, the moveable platform is positioned within a range that may be traveled by x-rays generated by the x-ray tube connected to the moveable platform. In this advantageous embodiment, the distance is a distance to a surface of the object to be inspected. The moveable platform may be positioned by a human operator, by operation of a motor, or another suitable method.

An x-ray beam is then generated using an x-ray tube (operation 802). The x-ray tube and a power supply are located inside of a housing connected to the moveable platform. The moveable platform is configured to move such that the housing and the x-ray tube in the housing move.

The process then rotates a rotatable wheel connected to the moveable platform while the x-ray beam is being generated (operation 804). The rotatable wheel has a number of apertures that allow at least a portion of the x-ray beam to pass through the rotatable wheel as the rotatable wheel rotates. The portion of the x-ray beam that passes through an aperture may be referred to as a collimated x-ray beam.

Further, the process moves the moveable platform while the rotatable wheel is rotating and the xray beam is being generated (operation 806). In this illustrative example, rotation of the rotatable wheel may be about an axis in which the moveable platform moves along a direction of this axis.

Thereafter, the process detects a backscatter in response to the collimated x-ray beam encountering a surface of an object (operation 808). In particular, the backscatter is formed by a portion of the x-rays in the collimated x-ray beam reflecting off of the surface of the object in response to the x-rays encountering the surface.

The process then generates a number of images in a grid-type pattern using the backscatter detected while the moveable platform is moving and the rotatable wheel is rotating (operation 810). The number of images may be generated in a grid-type pattern when the moveable platform is moved and the rotatable wheel is rotated at the same time while the x-rays are being generated by the x-ray tube. Next, the number of images are processed to determine whether a number of inconsistencies are present on the surface of the object (operation 812), with the process terminating thereafter.

In some alternative implementations of an advantageous embodiment, the function or functions noted in the block may occur out of the order noted in the figures. For example, in some cases, two blocks shown in succession may be executed substantially concurrently, or the blocks may sometimes be executed in the reverse order, depending upon the functionality involved. Also, other blocks may be added in addition to the illustrated blocks in a flowchart or block diagram.

Thus, the different advantageous embodiments provide a method and apparatus for generating x-rays. In one advantageous embodiment, an apparatus comprises a moveable platform, a housing connected to the moveable platform, a power supply located inside of the housing, an x-ray tube located inside of the housing, and a rotatable wheel connected to the moveable platform. The rotatable wheel has a number of apertures and is configured to rotate while the x-ray tube generates an x-ray beam such that the number of apertures allows at least a portion of the x-ray beam to pass through the rotatable wheel.

In this manner, the different advantageous embodiments provide an integrated backscatter x-ray system that has a reduced weight and/or size as compared to currently used x-ray systems that use backscattering. By including the power supply and a cooling system in the housing for the x-ray tube that generates the x-rays, the number of components needed for the x-ray systems may be reduced.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
   a moveable platform;
   a housing connected to the moveable platform;
   a power supply located inside of the housing;
   an x-ray tube located inside of the housing; and
   a rotatable wheel having a number of apertures, wherein the rotatable wheel is connected to the moveable platform and is configured to rotate while the x-ray tube generates an x-ray beam such that the number of apertures allow at least a portion of the x-ray beam to pass through the rotatable wheel, wherein the housing is positioned within an interior of the rotatable wheel.

2. The apparatus of claim 1 further comprising:
   a detector configured to detect a backscatter in response to the at least the portion of the x-ray beam encountering an object; and
   shielding around sections of the housing, wherein the shielding absorbs x-rays at locations on the housing at which the shielding is located.

3. The apparatus of claim 2, wherein the moveable platform is configured to move while the rotatable wheel rotates and the x-ray beam is being generated, and wherein the moveable platform is a cart.

4. The apparatus of claim 3, wherein the rotatable wheel is configured to rotate about an axis in which the moveable platform moves in a direction along the axis such that a number of images are generated in a grid-type pattern using the backscatter detected in response to the at least the portion of the x-ray beam encountering the object.

5. The apparatus of claim 1, wherein the x-ray tube comprises:
   a vacuum tube;
   a cathode located in the vacuum tube and configured to emit electrons; and
   a rotatable anode located in the vacuum tube and configured to be rotated by a motor located outside of the vacuum tube and is configured to generate x-rays in response to receiving the electrons emitted by the cathode.

6. The apparatus of claim 1, wherein the x-ray beam is a first x-ray beam that passes through a first window and wherein the x-ray tube is configured to generate a second x-ray beam that passes through a second window in which the first x-ray beam travels towards a first location on a surface of an object and the second x-ray beam travels towards a second location on the surface of the object.

7. The apparatus of claim 1, wherein the at least the portion of the x-ray beam passes through an aperture in the number of apertures as a collimated x-ray beam that travels towards a location on a surface of an object and wherein a portion of x-rays in the collimated x-ray beam is reflected off of the surface of the object.

8. The apparatus of claim 1, wherein the housing is a first housing, the power supply is a first power supply, the x-ray tube is a first x-ray tube, the x-ray beam is a first x-ray beam, and further comprising:
   a second housing connected to the moveable platform;
   a second power supply located inside of the housing; and
   a second x-ray tube located inside of the housing, wherein the second x-ray tube is configured to generate a second x-ray beam, and wherein the rotatable wheel is configured to allow the first x-ray beam to pass through the rotatable wheel to a first location on an object and allow the second x-ray beam to pass through the rotatable wheel to a second location on the object.

9. The apparatus of claim 8, wherein the object is a fuselage and the first location and the second location are inside the fuselage and wherein the first location is substantially opposite to the second location inside the fuselage.

10. The apparatus of claim 1 further comprising:
    a camera system configured to generate a number of images of an area around the housing and the moveable platform for use in moving the moveable platform in a number of directions.

11. The apparatus of claim 10, wherein the camera system is configured to generate the number of images using a backscatter detected in response to the at least the portion of the x-ray beam encountering a surface of an object.

12. The apparatus of claim 11, wherein the number of images are processed to determine whether a number of inconsistencies are present on the surface of the object.

13. A method for inspecting an object, the method comprising:
    positioning a moveable platform within a distance of the object to be inspected;
    generating an x-ray beam using an x-ray tube, wherein the x-ray tube and a power supply are located inside of a housing connected to a moveable platform, and wherein the x-ray beam travels the distance to the object;
    rotating a rotatable wheel connected to the moveable platform while the x-ray beam is being generated, wherein the rotatable wheel has a number of apertures that allow at least a portion of the x-ray beam to pass through the rotatable wheel as the rotatable wheel rotates, and wherein the housing is positioned within an interior of the rotatable wheel;
    detecting a backscatter in response to the at least the portion of the x-ray beam encountering the object, wherein the backscatter comprises x-rays in the at least the portion of the x-ray beam that are reflected off of a surface of the object; and
    generating a number of images using the backscatter for use in determining whether a number of inconsistencies are present on the surface of the object.

14. The method of claim 13, wherein the step of generating the x-ray beam using the x-ray tube comprises:
    emitting electrons using a cathode located in a vacuum tube; and
    rotating a rotatable anode in the vacuum tube, wherein the rotatable anode generates x-rays in response to receiving the electrons emitted by the cathode.

15. The method of claim 14, wherein the step of rotating the rotatable anode in the vacuum tube comprises:
    rotating the rotatable anode about an axis in which the moveable platform moves in a direction along the axis such that a number of images are generated for the object in a grid-type pattern.

16. The method of claim 13, wherein the moveable platform is a cart, wherein shielding is provided around sections of the housing, the shielding absorbing x-rays at locations on the housing at which the shielding is located, and the method further comprising: moving the moveable platform while the rotatable wheel rotates and while the x-ray beam is being generated.

17. The method of claim 16, wherein moving the moveable platform while the rotatable wheel rotates and while the x-ray beam is being generated comprises:
    generating a number of images of an area around the housing and the moveable platform using a camera system; and moving the moveable platform while the rotatable wheel rotates and while the x-ray beam is being generated using the number of images.

18. The method of claim 13, wherein the housing is a first housing, the power supply is a first power supply, the x-ray tube is a first x-ray tube, the x-ray beam is a first x-ray beam, and further comprising:

generating a second x-ray beam using a second x-ray tube, wherein the second x-ray tube and a second power supply are located inside of a second housing connected to the moveable platform; and rotating the rotatable wheel connected to the moveable platform while the x-ray beam is being generated, wherein the number of apertures allow at least a portion of the second x-ray beam to pass through the rotatable wheel as the rotatable wheel rotates.

19. The method of claim 13 further comprising:

cooling the x-ray tube and the power supply located in the housing a coolant present inside of the housing, wherein the x-ray tube and the power supply are immersed in the coolant inside of the housing.

20. The method of claim 13, wherein the object is a fuselage of a vehicle.

\* \* \* \* \*